(12) United States Patent
Pierro

(10) Patent No.: US 11,350,825 B2
(45) Date of Patent: Jun. 7, 2022

(54) CONTACTLESS SYSTEM AND METHOD FOR MEASURING AND CONTINUOUSLY MONITORING ARTERIAL BLOOD PRESSURE

(71) Applicant: Vivonics, Inc., Bedford, MA (US)

(72) Inventor: Michele Pierro, Medford, MA (US)

(73) Assignee: Vivonics, Inc., Bedford, MA (US)

( * ) Notice: Subject to any disclaimer, the term of this patent is extended or adjusted under 35 U.S.C. 154(b) by 749 days.

(21) Appl. No.: 15/685,477

(22) Filed: Aug. 24, 2017

(65) Prior Publication Data

US 2018/0055364 A1 Mar. 1, 2018

Related U.S. Application Data

(60) Provisional application No. 62/379,497, filed on Aug. 25, 2016.

(51) Int. Cl.
| | |
|---|---|
| A61B 5/00 | (2006.01) |
| A61B 5/053 | (2021.01) |
| A61B 5/021 | (2006.01) |
| A61B 5/024 | (2006.01) |
| A61B 5/0535 | (2021.01) |

(52) U.S. Cl.
CPC .......... *A61B 5/0059* (2013.01); *A61B 5/0006* (2013.01); *A61B 5/0077* (2013.01); *A61B 5/02125* (2013.01); *A61B 5/02416* (2013.01); *A61B 5/0535* (2013.01); *A61B 5/02108* (2013.01); *A61B 5/7235* (2013.01)

(58) Field of Classification Search
CPC ... A61B 5/0006; A61B 5/0059; A61B 5/0077; A61B 5/02108; A61B 5/02125; A61B 5/02416; A61B 5/0535; A61B 5/7235
See application file for complete search history.

(56) References Cited

U.S. PATENT DOCUMENTS

| | | |
|---|---|---|
| 9,125,606 B2 | 9/2015 | Verkruijsse et al. |
| 9,693,693 B2 | 7/2017 | Farag et al. |
| 2011/0178415 A1 | 7/2011 | Baldwin et al. |

(Continued)

OTHER PUBLICATIONS

Lamontagne et al., "Vasopressor Administration and Sepsis: A survey of Canadian Intensivists", Journal of Critical Care (2011) 26, pp. 532.e1-532.e7.

(Continued)

*Primary Examiner* — Michael T Rozanski
(74) *Attorney, Agent, or Firm* — Iandiorio Teska & Coleman, LLP

(57) ABSTRACT

A contactless system for measuring and continuously monitoring arterial blood pressure includes a light source configured to illuminate light having at least one predetermined wavelength at a predetermined area of a human subject having an artery therein. A detector responsive to reflected light from the predetermined area to continuously acquire images of the artery in the predetermined area. A processor processes the images and determines when an image at a proximal location of the predetermined area is darker indicating transition of a pulse wave into the artery at the proximal location and at a proximal time and when an image at a distal location of the predetermined area is darker indicating transition of the pulse wave into the artery at a distal location at a distal time to contactlessly and continuously calculate the arterial blood pressure for each cardiac cycle of the human subject.

17 Claims, 8 Drawing Sheets

(56) References Cited

U.S. PATENT DOCUMENTS

2011/0196244 A1 8/2011 Ribas Ripoll et al.
2015/0018637 A1 1/2015 Chen et al.
2015/0287187 A1 10/2015 Redtel
2016/0058409 A1 3/2016 Mizukami
2016/0206219 A1 7/2016 Fortin

OTHER PUBLICATIONS

Magder, S., Point: Counterpoint Comments, "Point: The classical Guyton view that mean systemic pressure, right atrial pressure, and venous resistance govern venous return is/is not correct." J. Appl. Physiol. (2006) 101: 1528-1530.
Peterson, et al., "Mechanical Properties of Arteries in Vivo", Circulation Research, VIII, May 1960, pp. 622-639.
Written Opinion of the International Searching Authority for International Application No. PCT/US2017/48550 dated Nov. 7, 2017 (four (4) pages).
Magder, S., Point: Counterpoint Comments, "Point: The classical Guyton view that mean systemic pressure, right atriai pressure, and venous resistance govern venous return is/is not correct." J. Appl. Physiol. (2006) 101: 1528-1530.

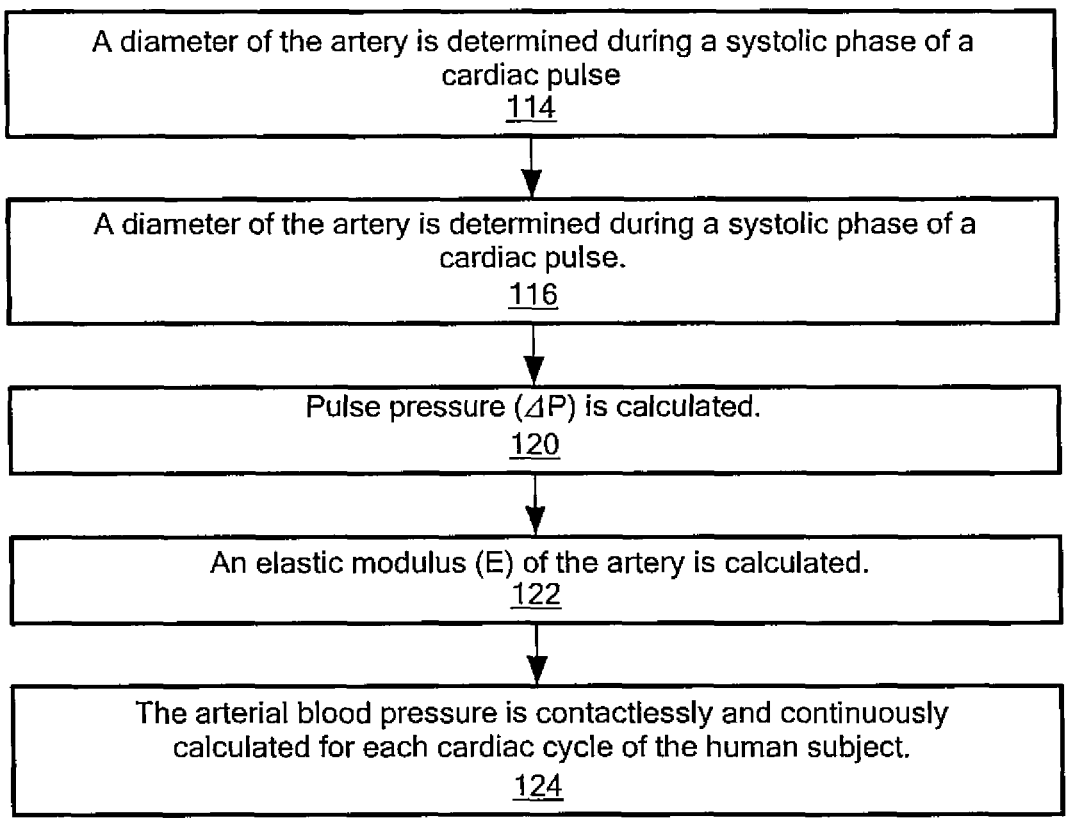
FIG. 7 (Con't)

CONTACTLESS SYSTEM AND METHOD FOR MEASURING AND CONTINUOUSLY MONITORING ARTERIAL BLOOD PRESSURE

RELATED APPLICATIONS

This application claims benefit of and priority to U.S. Provisional Application Ser. No. 62/379,497 filed Aug. 25, 2016 under 35 U.S.C. §§119, 120, 363, 365, and 37 C.F.R. §1.55 and §1.78 which is incorporated herein by this reference.

FIELD OF THE INVENTION

This invention relates to a contactless system and method for measuring and continuously monitoring arterial blood pressure.

BACKGROUND OF THE INVENTION

Arterial blood pressure measurement is one of the most basic clinical procedures performed by healthcare workers in a variety of situations, ranging from urgent care to routine check controls. Minimal values for arterial blood pressure are often targeted for critically ill patients. See, e.g., *Vassopressor administration and sepsis: A survey of Canadian intensivists*, Lamontagne et al., J. Crit. Care 2011; 26:532, incorporated by reference herein.

Blood pressure (BP) is the force that distends the elastic walls of the blood vessels. Physical measurements are actually relative measurements since they are referred to some reference value. The human body is surrounded by atmospheric pressure, thus measurement of arterial blood pressure is presented as a deviation from atmospheric pressure, which is defined as the zero value. Arterial blood pressure is created by the volume per time that the heart forces blood through the systemic vascular resistance. See, e.g., *The classical Guyton view that mean systemic pressure, right atrial pressure, and venous resistance govern venous return is correct*, Magder S., and Point, J. Appl. Physiol (1985) 2006, 101:1523-1525, incorporated by reference herein. While the pulsatile component of the arterial pressure is originated by the cyclic contraction of the heart, the determinants of the systolic and diastolic pressure are far more complex. When the stroke volume is pumped into the elastic aorta, the aortic wall is stretched and part of the volume is temporarily taken up by the aorta to be the released during the rest of the cycle. Such transmissible pressure is commonly designated by an arterial pressure pulse wave (PW), which appears as a waveform with specific amplitude features dictated by the systolic and diastolic blood pressure values. Under normal flow conditions the PW is amplified when measured further away from the aorta, although there is a slight decrease in mean pressure. Furthermore, the contour of a PW is determined by a variety of other factors, e.g., age, weight, physical conditions, vascular health status, drug administration, and the like.

One of the most accurate conventional measurements for measuring arterial BP may be achieved invasively using an arterial line. One conventional invasive arterial BP measurement system utilizes an intravascular cannula to provide a direct measurement of arterial pressure by placing a cannula needle in an artery, such as the radial artery, the femoral artery, the *dorsalis* artery or the branchial artery. The cannula needs to be connected to a sterile, fluid-filled system, which is connected to an electronic pressure transducer.

One advantage of such a conventional arterial BP measurement system, particularly in patients that require intensive care, is that arterial BP is constantly monitored beat-by-beat and a waveform, represented as a graph of pressure against time, is displayed on a screen for the medical professionals to see and perform real-time evaluations.

However, despite their accuracy, conventional invasive arterial BP measurement systems are generally used only in hospitals, especially in intensive care units, since they are known to carry risks associated with complications, such as thrombosis, infection, bleeding, and the like. Additionally, patients having invasive arterial monitoring associated with invasive arterial BP measurement systems require very close supervision because there is a danger of severe bleeding if the line becomes disconnected.

Conventional photoplethysmography (PPG) systems and methods, which employ optical transmittance or reflectance to measure waveforms indicative of proximal and distal blood volume oscillations, have been widely employed for monitoring cardiovascular activity. Light intensity resulting from temporal fluctuations in local blood volume translates into waveforms meaningful for cardiovascular activity monitoring. Conventional PPG systems and methods have been used to assess cardiovascular factors such as heart rate, blood oxygen saturation, and peripheral vascular disease based on blood pressure measurements.

However, conventional PPG systems and methods may be limited to single patient monitoring and confine the number of simultaneous cardiovascular related measurements that can be achieved. Additionally, conventional PPG systems and methods rely on directly contacting the skin of the patient which may prevent its use in monitoring applications for patients with exposed wounds or burns in patients with particularly delicate and sensitive skin, such as neonates or similar type patients where contacting the skin is problematic. Conventional contact PPG systems and methods, in addition to being cumbersome because of wires and cable necessary for the data acquisition, are also significantly affected by relative motion between the skin and the sensors resulting in poor signals quality.

SUMMARY OF INVENTION

In one aspect, a contactless system for measuring and continuously monitoring arterial blood pressure is featured. The system includes a light source configured to illuminate light having at least one predetermined wavelength at a predetermined area of a human subject having an artery therein. A detector responsive to reflected light from the predetermined area is configured to continuously acquire images of the artery in the predetermined area. A processor is configured to process the images and determine when an image at a proximal location of the predetermined area is darker indicating transition of a pulse wave into the artery at the proximal location and at a proximal time and an image at a distal location of the predetermined area is darker indicating transition of the pulse wave into the artery at a distal location at a distal time, determine the difference in time between the distal time and the proximal time to calculate a pulse transit time (PTT), determine a length between the proximal location and the distal location, determine a diameter of the artery during a systolic phase of a cardiac pulse, determine a diameter of the artery during a diastolic phase of a cardiac pulse, calculate a pulse wave velocity of the pulse wave, calculate pulse pressure ($\Delta P$), calculate an elastic modulus (E) of the artery, and contactlessly and continuously calculate the arterial blood pressure for each cardiac cycle of the human subject.

In one embodiment, the at least one predetermined wavelength may include one or more wavelengths between a wavelength of green light and a wavelength of near infrared (NIR) light. The predetermined wavelength may be sensitive to oxygenated and/or deoxygenated hemoglobin concentration in blood of the human subject. The light source may include one or more near infrared (NIR) sensors. The detector may include a charge coupled device (CCD) camera. The system may include a plurality of light emitting devices configured to provide the distal proximal location and the distal location. The system may include a storage device coupled to the processor. The system may include a display coupled to the processor configured to continuously display measured arterial blood pressure for each cardiac cycle. The system may include a user interface coupled to the display.

In another aspect, a method for continuously measuring and continuously monitoring arterial blood pressure is featured. The method includes illuminating light at at least one predetermined wavelength at a predetermined area of a human subject having an artery therein, continuously acquiring images of the artery in the predetermined area from light reflected from the predetermined area, processing the images with a processor to determine when an image at a proximal location of the predetermined area is darker indicating transition of a pulse wave into the artery at the proximal location and at a proximal time and when an image at a distal location of the predetermined area is darker indicating transition of the pulse wave into the artery at a distal location at a distal time, determine the difference in time between the distal time and the proximal time to calculate a pulse transit time (PIT), determine a length between the proximal location and the distal location, calculate a pulse wave velocity of the pulse wave, determine a diameter of the artery during a diastolic phase of a cardiac pulse, determine a diameter of the artery during a diastolic phase of a cardiac pulse, calculate pulse pressure (ΔP), calculate an elastic modulus (E) of the artery, and contactlessly and continuously calculate the arterial blood pressure for each cardiac cycle of the human subject.

In another embodiment, the at least one predetermined wavelength may include one or more wavelengths between a wavelength of green light and a wavelength of near infrared (NIR) light. The predetermined wavelength may be sensitive to oxygenated and/or deoxygenated hemoglobin concentration in blood of the human subject. The illuminating light may be provided by one or more near infrared sensors. The method may include providing a plurality of light emitting devices configured to provide the distal proximal location and the distal location. The method may include continuously displaying the measured arterial blood pressure.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
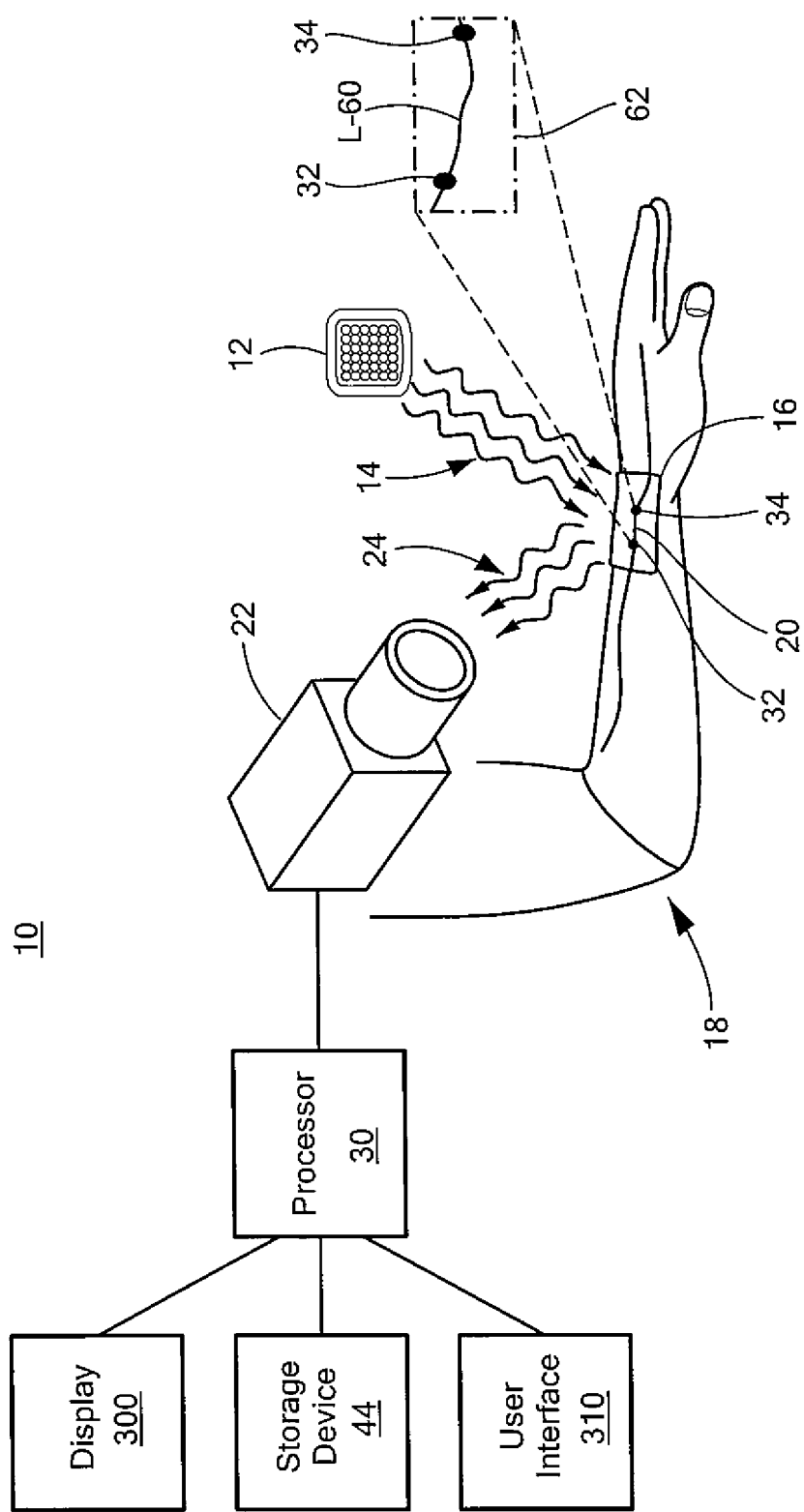
FIG. 1 is a schematic diagram showing the primary components of one embodiment of the contactless system and method for measuring and continuously monitoring arterial blood pressure of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

As discussed in the Background section above, conventional invasive arterial BP measurement systems which rely on placing a cannula needle in an artery are typically only used in a hospital or similar type setting because of risks associated therewith. Additionally, patients utilizing such conventional invasive arterial BP measurement systems require close supervision because of the danger from severe bleeding if the line becomes disconnected.

Conventional photoplethysmography (PPG) systems and methods which utilize optical transmittance or reflectance to measure waveforms indicative of proximal and distal volume oscillations are typically limited to single patient monitoring and rely on directly contacting the skin of the patient. Thus, conventional photoplethysmography (PPG) systems and methods may not be used with patients having exposed to wounds or burns, patients with delicate or sensitive skin, or similar type patients where contacting the skin is problematic.

There is shown in FIG. 1, one embodiment of the contactless system 10 for measuring and continuously monitoring arterial blood pressure of this invention. System 10 includes one or more light sources 12 configured to illuminate light 14 having at least one predetermined wavelength at a predetermined area of a human subject having an artery therein. In this example, predetermined area 16 is located on arm 18 of a human subject having artery 20 therein. In other examples, predetermined area 16 may be any desired area of the human subject having an artery therein, such an area of the human subject having the left or right radial artery, the ulna artery, the brachial artery, the femoral artery, the tibial artery, the carotid artery, or similar type artery therein. In one example, one or more light sources 12 may be one or more near infrared (NIR) sensors preferably configured to emit one or more wavelengths between the wavelength of green light (e.g., about 510 nm) and the wavelength of near infrared (NIR) light (e.g., about 700 nm). In one example, the preferred wavelength of light emitted by one or more light sources 12 may be about 850 nm, as the chromophores in artery 20 absorbed light better at this wavelength. In this example, the wavelength of light 14 illuminated by one or more light sources 12 is preferably sensitive to changes in oxygenated and/or deoxygenated hemoglobin concentration in the blood in artery 20.

System 10 also includes detector 22 responsive to reflected light 24 from light 14 illuminated on predetermined area 16 having artery 20 therein. Detector 22 is configured to continuously acquire images of artery 20 in predetermined area 16. In one example, detector 22 is a charge coupled device (CCD) camera or similar type device.

Light 14 illuminated from one or more light sources 12 preferably probes a portion of the tissue, e.g., the skin of the human subject in predetermined area 16, allowing light 14 to integrate one or multiple vascular pathways, e.g., artery 20. From reflected light 24, detector 22 visualizes the structure of the skin, blood vessels, and thus the structure of artery 20 and evaluates arterial pulsations and dynamic changes of arterial profusion. Images of pulse wave 38, FIGS. 2, 3 and 4 propagating through the artery 20, FIGS. 2 and 3, in predetermined area 16 at each cardiac cycle, e.g., in the direction indicated by arrows 76, are captured by detector 22 and sent to processor 30. Detector 22, may include sensors having analog amplifiers and filters to increase gain of the signal and reduce background noise to create clean images. To reduce and minimize impact of uncontrolled ambient light changes, system 10 may implement spectral estimation techniques of ambient illumination and then remove it. System 10 may also remove ambient lighting artifacts at the acquisition level by removing temporal changes in ambient illumination measured during program periods of non-active tissue illumination.

System 10 also includes processor 30, FIG. 1, configured to process the images and determine when an image at proximal location 32 of predetermined area 16 is darker indicating a transition of a pulse wave into artery 20 at proximal location 32 and at a proximal time and when an image at distal location 34 of predetermined area 16 is darker indicating transition of the pulse wave into artery 20 at distal location 34 at a distal time.

Figure 2:
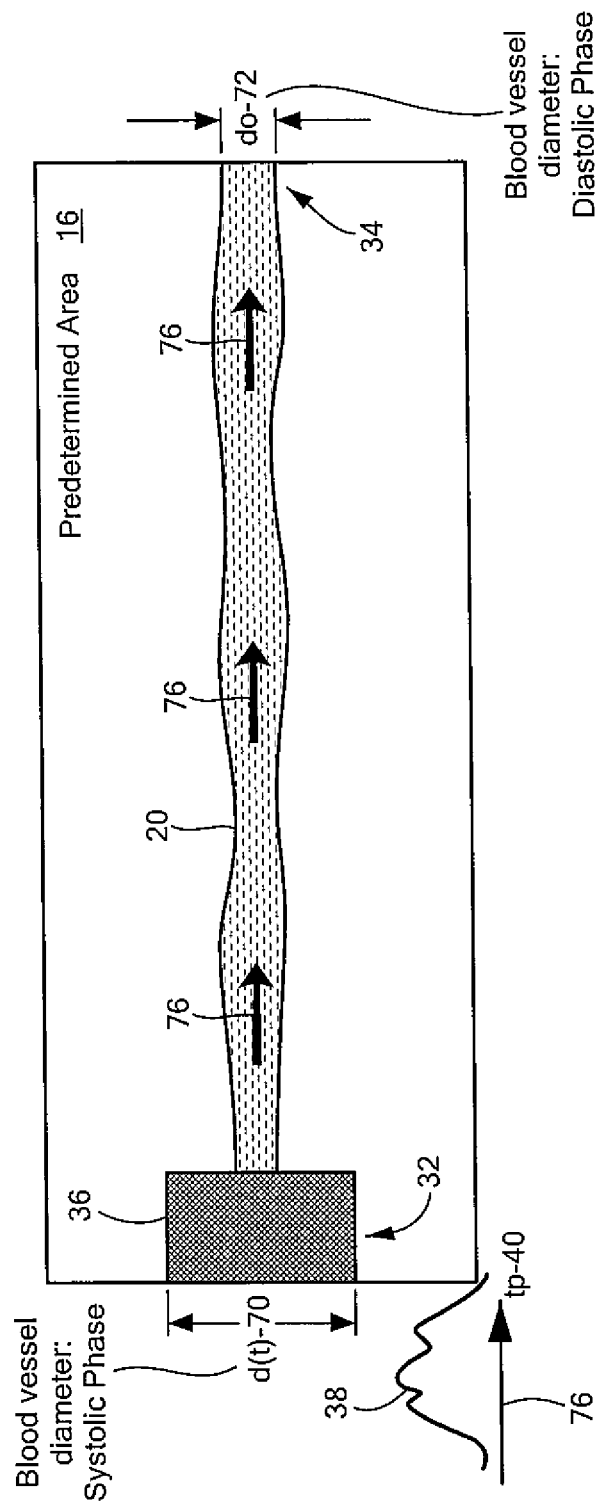
FIG. 2 is a schematic diagram showing in further detail the predetermined area shown in FIG. 1 and the artery therein and also showing an example of a darker image with higher light absorption due to the blood volume oscillation associated with the pulse wave propagation at a proximal location in the predetermined area indicating transition of a pulse wave into the artery at the proximal location.

For example, FIG. 2 shows in further detail predetermined area 16 with artery 20 therein. Processor 30 determines when image 36 at proximal location 32 is darker as shown indicating transition of pulse wave 38 into artery 20 at proximal location 32 and at proximal time tp-40. As known by those skilled in the art, when artery 20 is fully expanded during a systolic phase of cardiac cycle, the absorption property of the tissue artery 20 changes which and creates a darker image when compared to artery 20 being in a less expanded state, e.g., during the diastolic phase of a cardiac cycle, where the absorption property of the tissue artery 20 creates a lighter image. Similarly, Processor 30 determines when image 42, FIG. 3, at distal location 34 of predetermined area 16 is darker as shown indicating transition of pulse wave 38 into artery 20 at distal location 34 at distal time td-46. FIG. 4 shows in further detail pulse wave 38 showing systolic blood pressure (BP) indicated at 46 and diastolic blood pressure (BP) indicated at 48

Processor 30 may be configured as one or more processors, an application-specific integrated circuit (ASIC), firmware, hardware, and/or software (including firmware, resident software, microcode, and the like), or a combination of both hardware and software that may be all generally referred to as a processor. Computer code for the programs carrying out the instructions or operations of processor 30 of one or more embodiments of this invention may be written in any combination of one or more programming languages including an object oriented programming language, such as $C^{++}$, Small Talk, Java, and the like, or conventional procedural programming languages, such as "C" programming language, or similar programming languages, or in an assembly code. The computer program instructions may also be stored, 30, in a computer-readable medium, e.g., storage 44 (discussed below), that can direct a computer, other programmable data processing apparatus, or other devices to function in a particular manner, such that the instructions stored in the computer-readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer-implemented process such that the instructions which execute on the computer or other programmable apparatus provide processes for implementing the functions/acts specified in the flowchart and/or block diagram block or blocks disclosed herein.

System 10 also preferably includes storage device 44, FIG. 1, e.g. a computer-readable storage medium or memory, such as an electronic, magnetic, optical, electromagnetic, infrared, or semiconductor system, apparatus, or device, or any suitable combination of the foregoing. Other examples of storage 44 may include an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. As disclosed herein, the computer-readable storage medium or memory of storage device 44 may be any tangible medium that can contain, or store one or more programs for use by or in connection with processor 30.

Figure 3:
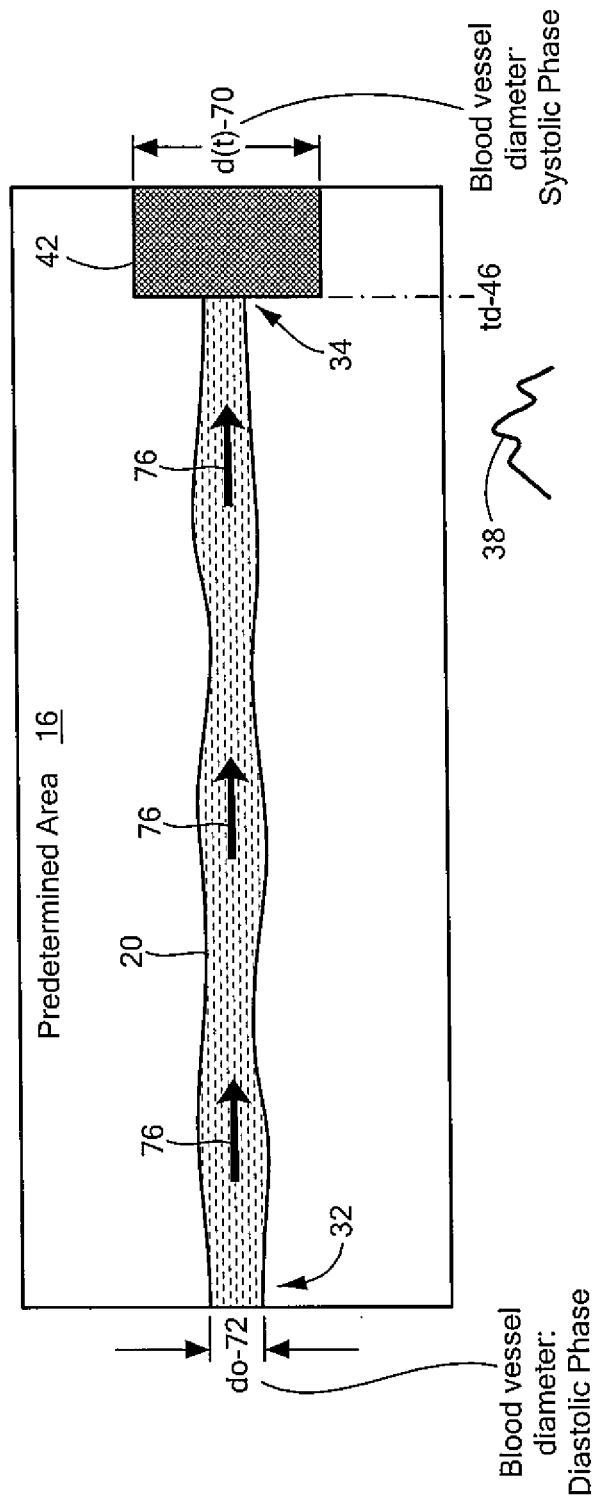
FIG. 3 is a schematic diagram showing in further detail the predetermined area shown in FIG. 1 and the artery therein and also showing an example of a darker image with higher light absorption due to the blood volume oscillation associated with the pulse wave propagation at a distal location in the predetermined area indicating transition of a pulse wave into the artery at the distal location.
Figure 4:
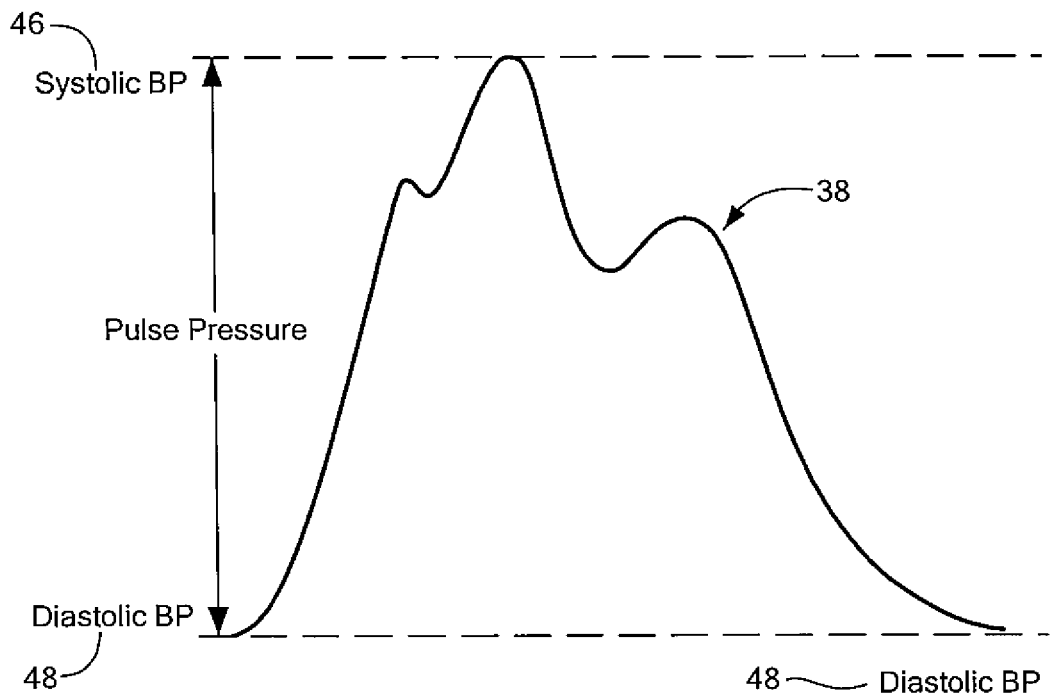
FIG. 4 is a graph showing in further detail the pulse pressure waveform shown in FIGS. 2 and 3.

Processor 30, FIG. 1, is configured to determine the difference in time between distal time td-46, FIG. 3, and proximal time tp-40, FIG, 2, to calculate pulse transit time (PTT). Arterial pulsations of artery 20 and dynamic changes captured by detector 22, FIG. 1, from light 24 reflected from artery 20 of predetermined area 16 allow for the calculation of PTT, which is the delay between pressure waveform 38, FIG. 2, captured at proximal location 32, FIG. 2, at proximal time tp-40 and pressure waveform 38, FIG. 3, captured at distal location 34 at distal time td-46, FIG. 3.

Processor 30 is also configured to determine a length L-60, FIG. 1, shown in caption 62, between proximal location 32 and distal location 34. In one example, system 10 may utilize light emitting device 64, FIG. 5, configured to emit spaced light 66 and 67 to create reference object 68 and reference object 70 on artery 20 in predetermined area 16. Reference objects 68 and 70 are detected by detector 22, FIG. 1. Processor 30 then determines length L-60. In one example, light emitting device 64 may be two spaced laser pointers.

Figure 5:
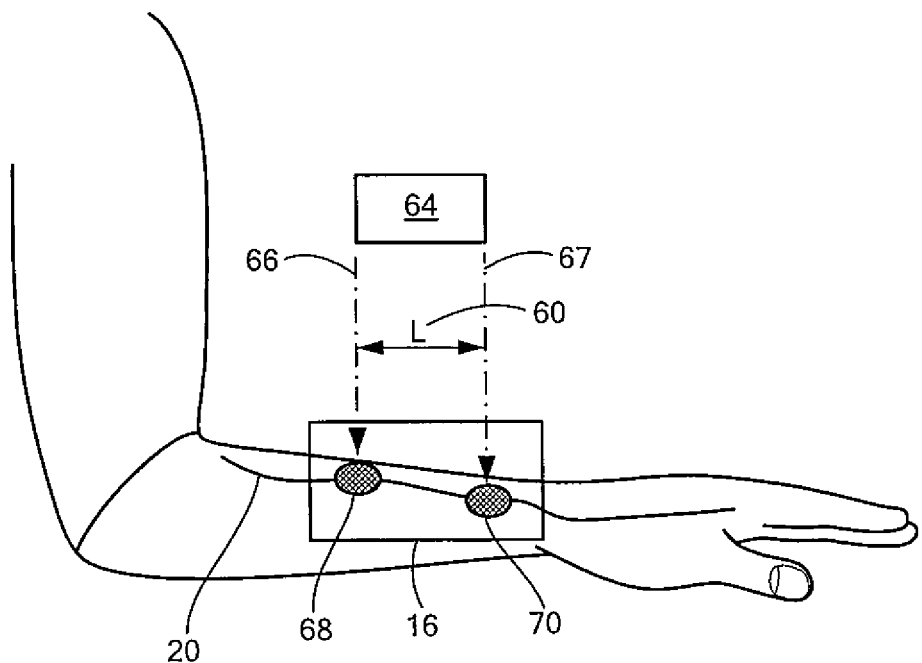
FIG. 5 is a schematic diagram showing an example of light emitting devices which may be used to create reference objects in the predetermined area shown in FIGS. 1-3 in order to calculate the length between the proximal location and the distal location shown in FIGS. 1-3.

Once L-60, FIGS. 1 and 5 is determined, processor 30 translates the calculated pulse transit time (PTT) into pulse wave velocities (PWV) in accordance with the equation:

$$PWV = \frac{L}{PTT} \quad (1)$$

Processor 30, FIG. 1, then determines a diameter of artery 20, FIGS. 1-3 during a systolic phase of a cardiac pulse and the diameter of artery 20 during a diastolic phase of the cardiac pulse. For example, FIG. 2 shows an example of diameter d(t)-70 determined by processor 30, shown in greater detail in FIG. 6, of artery 20 at proximal location 32, FIG. 2, and at proximal time tp-40, during a systolic phase of a cardiac cycle when artery 20 is expanded due to the systolic phase of the cardiac cycle. FIG. 2 also shows an example of diameter do-72, shown in greater detail in FIG. 6, determined by processor 30, of artery 20 at distal location 34 during a diastolic phase of a cardiac cycle when artery 20 is less expanded during the diastolic phase of the cardiac cycle. Similarly, FIG. 3 shows an example of diameter d(t)-70 determined by processor 30 of artery 20 at distal location 34 location and in this example, at distal time td-46, during a systolic phase of a cardiac cycle when artery 20 is expanded due to the systolic phase of the cardiac cycle. FIG. 3 also shows an example of diameter do-72 of artery 20, in this example at proximal location 32, during a diastolic phase of a cardiac cycle when artery 20 is less expanded during the diastolic phase of the cardiac cycle.

Processor 30, FIG. 1, is then configured to calculate pulse pressure (ΔP) and the elastic modulus (E) of artery 20. From the pulse wave velocity (PWV) shown in equation (1), the pressure gradient corresponding to the difference between the maximum and minimum pressure during the cardiac cycle can be calculated by processor 30 using the following equation:

$$PWV = \sqrt{\frac{\Delta PV}{\Delta V \varphi}} \quad (2)$$

where V and ΔV are the luminal volume and the difference between maximum and minimum volume during the cardiac cycle, respectively, and φ is the blood density, e.g., about 1059 kg m$^{-3}$. V and ΔV respectively are estimated by change in diameter size of the imaged artery 20 as pressure wave 38, FIGS. 2 and 3, propagates though artery 20 in the direction indicated by arrows 76, e.g., the difference between diameter d(t)-70, FIGS. 2, 3, and 6, of artery 20 during the systolic phase of the cardiac cycle and diameter do-72 of artery 20 during the diastolic phase of a cardiac cycle. The pulse pressure (ΔP) is related to the elastic modulus (E) as the ratio of stress to strain in terms of the pulse pressure and directly measurable artery diameter parameters ΔD and D. This relationship may be represented by the following expression:

$$E = \frac{\Delta P}{\Delta D/D} \quad (3)$$

By replacing ΔP from equation (2) into equation (3) the elastic modulus (E) of artery 20 is calculated by processor 30 using equation (3).

Figure 6:
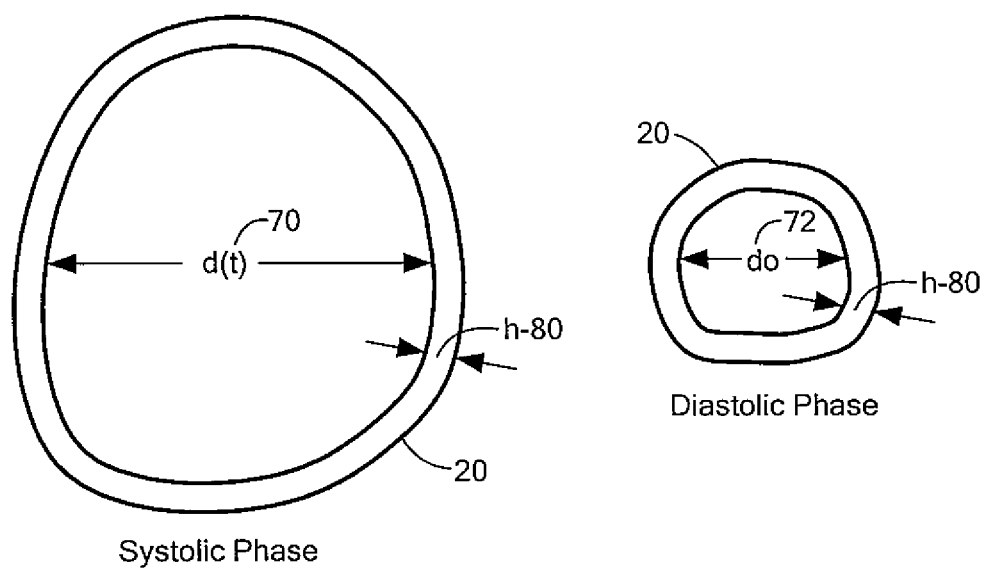
FIG. 6 shows examples of the diameter of artery 20 shown in FIGS. 1-3 during a systolic phase of a cardiac cycle and a diastolic phase of a cardiac cycle.

Processor 30 then contactlessly and continuously calculates or measures the arterial blood pressure, p(t), for each cardiac cycle of the human subject in accordance with the following equation:

$$p(t) = \frac{Ed(t)h}{d_0(1-\theta^2)} \quad (4)$$

where d(t) in equation (4) is d(t)-70, FIGS. 2, 3, and 6 of artery 20 during the systolic phase of the cardiac cycle as discussed above, $d_o$ is diameter do-72 of artery 20 during the diastolic phase of a cardiac cycle as discussed above, h is the thickness of the wall of artery 20, indicated at 80, FIG. 6, and θ is the Poisson's ratio, ideally about 0.5.

Figure 7:
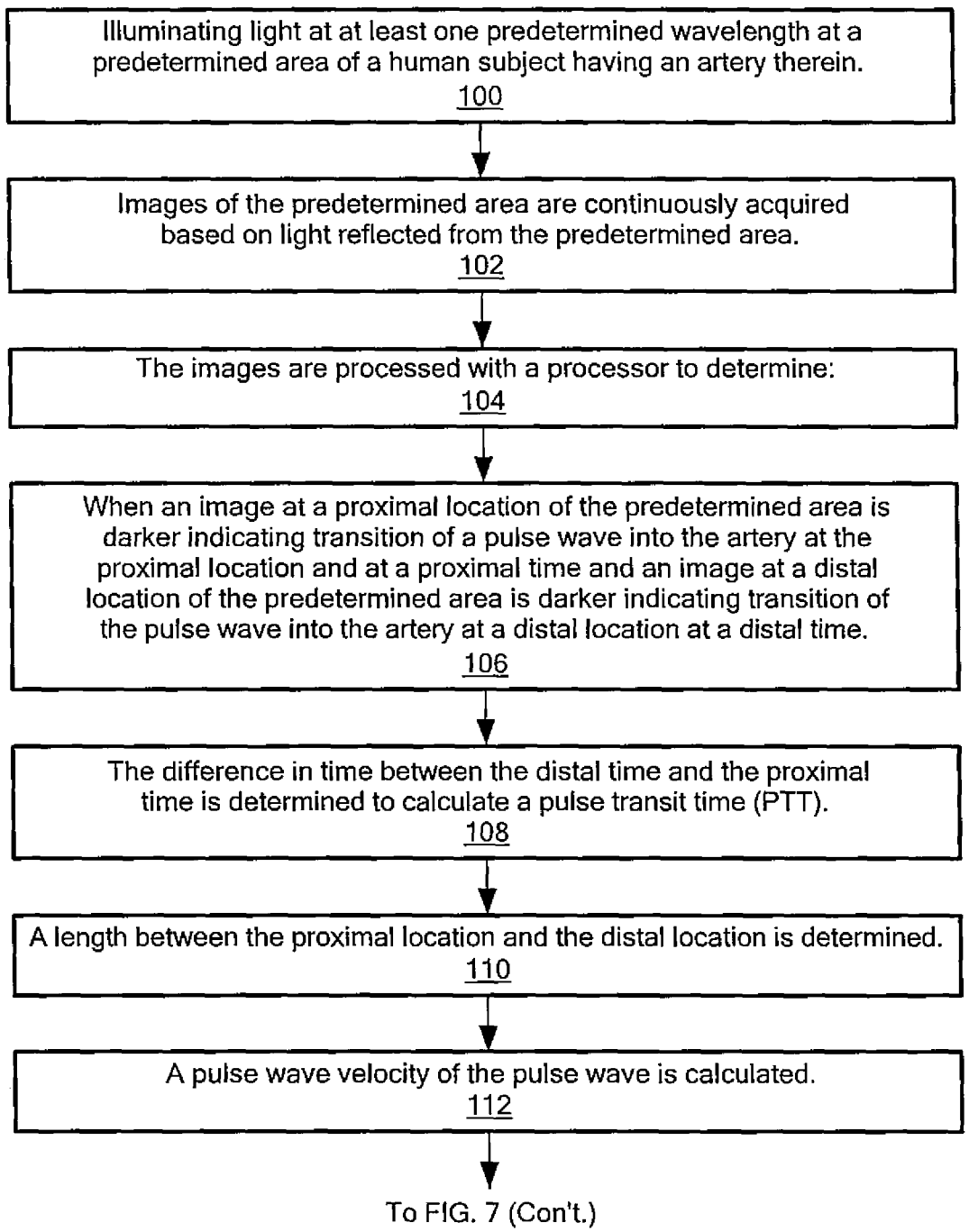
FIG. 7 is a block diagram showing on example of the primary steps of one embodiment of the method for contactless measuring and continuously monitoring arterial blood pressure of this invention.

FIG. 7 shows one exemplary flowchart of the method for measuring and continuously monitoring arterial blood pressure of one embodiment of this invention. In this example, the method includes illuminating light having at least one predetermined wavelength at a predetermined area of a human subject having an artery therein, step 100. Images of the predetermined area are continuously acquired based on the light reflected from the predetermined area, step 102. The images are then processed with processor 30, FIG. 1, step 104, FIG. 7, to determine when an image at a proximal location of the predetermined area is darker indicating transition of a pulse wave into the artery at the proximal location and at a proximal time and when an image at a distal location of the predetermined area is darker indicating transition of a pulse wave into the artery at the distal location at the distal time, step 106. Processor 30 then determines the difference in time between the distal time and the proximal time to calculate a pulse transit time, step 108. Processor 30 then determines a length between the proximal location and the distal location, step 110. Processor 30 then calculates the pulse wave velocity, step 112. Processor 30 then determines a diameter of the artery during a systolic phase of a cardiac pulse, step 114. Processor 30 then determines a diameter of an artery during a diastolic phase of a cardiac pulse, step 116. Processor 30 then calculates pressure pulse (ΔP), step 120. Processor 30 then calculates an elastic modulus (E) of the artery, step 122. Processor 30 then contactlessly and continuously calculates or measures the arterial blood pressure (BP) for each cardiac cycle of the human subject, step 124. System 10, FIG. 1, also preferably includes display 300, FIG. 1, configured to continuously display the measured arterial blood pressure.

Figure 8:
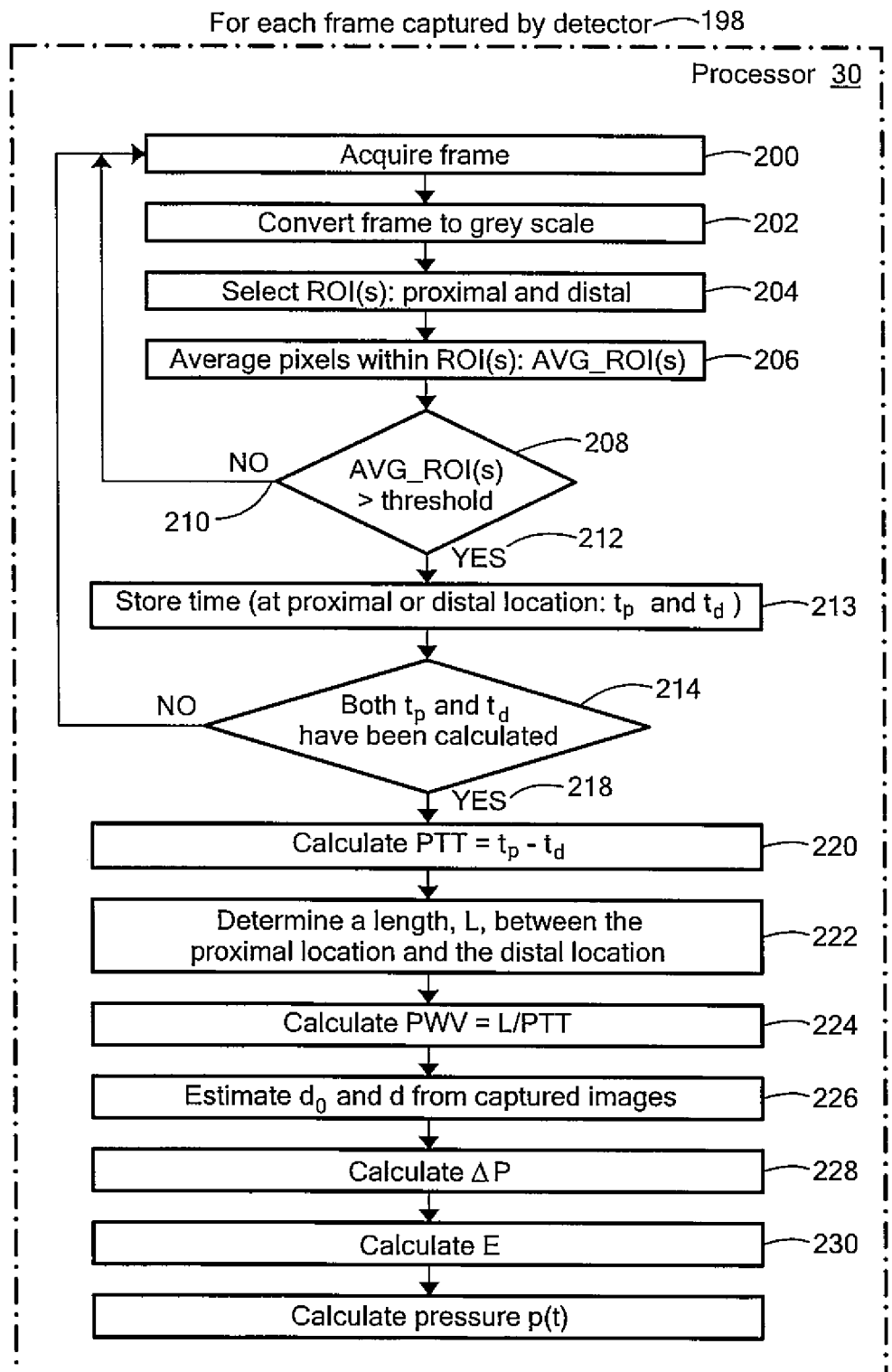
FIG. 8 is a flowchart showing in further detail one example of the contactless system and method for measuring and continuously monitoring arterial blood pressure shown in one or more of FIGS. 1-7.

FIG. 8 shows one example of a flowchart of system 10 and the method thereof shown in one or more of FIGS. 1-7 for contactlessly measuring and continuously monitoring arterial blood pressure. In this example, for each frame captured by detection device 12, FIG. 1, indicated at 198, FIG. 8, processor 30, FIG. 1, acquires a frame, step 200, FIG. 8, The frame is converted to grayscale by processor 30, step 202. One or more regions of interest (ROI(s)), or predetermined area 16, FIGS. 1-3 and 5, is selected having proximal location 32 and distal location 34, step 204, FIG. 7. The average of the pixels within the region of interest or predetermined area 16 is then determined, step 206. A decision is made if the average of the pixels within the region of interest or predetermined area 16 is greater than a predetermined threshold, step 208. if NO, indicated at 210. Steps 200-208 are repeated. If YES, indicated at 212, then time the proximal time, tp-40, FIG. 2, that the pulse wave 38 enters proximal location 32 of artery 20 or the distal time, td-46, FIG. 3, that pulse wave 38 enters distal location 34 are stored, e.g., to storage device 44, FIG. 1, step 212, FIG. 8. A determination is then made that both proximal time, tp-40, and distal time, td-46, have been calculated, step 214, If NO, indicated at 216, steps 200-214 are repeated. If YES, indicated at 218, the difference in time between distal time, td-46, FIG. 3, and proximal time 43-40, FIG. 2, is determined to calculate pulse transit time (PTT), step 220. The difference in length, L-60, FIGS. I and 5, between proximal location 32 and distal location 34, FIGS. 1-3 and 5, is then determined by processor 30, step 222, FIG. 8. The pulse wave velocity (PWV) is then calculated by processor 30 using equation (2) above, step 224, An estimate of the initial diameter do-72, FIGS. 2 and 3, of artery 20 during the diastolic phase of a cardiac cycle and diameter d(t)-70 during the systolic phase of a cardiac cycle is then calculated by processor 30 from the captured images acquired by detector 22, step 226. The pulse pressure (ΔP) of artery 20, FIGS. 1-3 is then calculated by processor 30, step 228. The elastic modulus (E) of artery 20 is then calculated by processor 30, step 230, e.g., using equation (3) above, The arterial blood pressure, p(t), is then co tactlessly and continuously calculated or measured by processor 30 for each cardiac cycle of the human subject, step 230. e,g., using equation (4) above.

System 10, FIG. 1, also preferably includes user interface 310 configured to allow a user of system 10 to access and interact with processor 30, storage device 44, and display 300.

In one design, system 10 shown in one or more of FIGS. 1-7, may be integrated into electronic or mobile device having a processor therein. System 10 and the method thereof may be a standalone device, strap-on device, a wearable device, smart watch, or similar type device or integrated into wearable tools worn by medical professionals or worn directly on the human subject.

The result is system 10 and the method thereof contactlessly and continuously measures arterial blood pressure for each cardiac cycle of the human subject. Thus, system 10 can be used on patients with exposed wounds or burns, patients with delicate or sensitive skin, such as neonates, or similar type patients where contacting the skin is problematic. Moreover, system 10 and the method thereof reduces the risks associated with conventional invasive arterial blood pressure measurement systems, e.g., thrombosis, infection, bleeding, and the like. System 10 and the method thereof also eliminates the need for close supervision for patients which may be as risk for damage of severe bleeding if a cannula line becomes disconnected. Additionally, system 10 and the method thereof may provide for long distance measurements with multiple light sources and detectors mounted in a room to perform continuous monitoring of multiple patients in the room. The contactless, long distance, hemodynamic measurements and continuous monitoring provides for use in settings where multiple individual assessments may be difficult or not feasible, e.g., in intensive care units, emergency rooms, and the like. Additionally, system 10 and the method thereof may simplify network infrastructure because system 10 requires minimal wires and/or cables.

For enablement purposes only, the following code portions are provided which can be executed on processor 30, one or more processors, a computing device, or computer to carry out the primary steps and/or functions of contactless system 10 and the method thereof for continuously measuring and monitoring arterial blood pressure of this invention as discussed above with reference to one or more of FIGS. 1-8 and recited in the claims hereof. Other equivalent algorithms and code can be designed by a software engineer and/or programmer skilled in the art using the information provided herein.

The following pseudo code assumes that images, acquired from detector 22, FIG. 1, e.g., a camera, will be provided at a sampling rate (fps) at least twice the cardiac frequency specific for the investigated human subject (or patient).

```
//This function performs a calibration using a reference object of known dimensions. It
calculates a ratio, herein called pixel per metrics, which in turn can be used to estimate
the size of any objects in the acquired image:
measureSizeOfReferenceObject( ):
        // Sort object contours and define pixel_per_metrics; i.e. # of pixels per every
        inch/mm etc.
        pixel_per_metrics = objectWidth / knowWidth
        return pixel_per_metrics
//This function calculate the blood vessel diameter size during the systolic or diastolic
phase:
calculateArteryDiameter( ):
        //Smooth image
        smoothedImage = GaussianFilter( frame )
        //Detect blood vessel edges:
        Edges = edgeDetection( smoothedImage )
        // number of pixels within edges (done perpendicularly to the artery largest
        dimension)
        pixelsNumber = findPixelNumber ( Edges )
        //use pixel_per_metrics to assess artery diameter
        diameter = pixelsNumber / pixel_per_metrics
        return diameter
main( ):
        // declare and define counter for time tracking purposes:
        counter = 0
```

```
// declare and define threshold for peaks identification
threshold = threshold_value;
Tp = Td = 0
//select proximal and distal ROI: input by the user or declared before run time
proximalROI = pixel coordinates for proximal ROI
distalROI    = pixel coordinates for distal ROI
// measure the size of a reference object (this can be done on the first acquired
frame)
pixel_per_metrics = measureSizeOfReferenceObject( firstAcquiredFrame )
// as images keep on being available
while frame is different from NULL:
        capture frame //as provided by camera
        if capture frame is different from gray scale
                convert frame to gray scale
        else
                //do nothing
        end
// Average pixel values within ROIs of selected frame, which defines the
contactless PPG signals:
AVG_proximalROI (t) = mean ( proximalROI )
AVG_distalROI (t)   = mean ( distalROI )
// find the peaks on PPG signals if at least three seconds of data have been
collected; this should assure at least two cardiac cycles:
If counter >= 3*sampling rate
        // find the peaks for both signals: AVG_proximalROI and AVG_
distalROI:
        // if PPG signals instantaneous value is greater than defined
threshold:
        If AVG_proximalROI (t) > threshold
                // store waveform propagation-time at proximal location
                Tp = t
                // estimate extended artery's diameter during systolic phase
                d = calculateArteryDiameter ( frame, pixel_per_metrics )
        end
        If AVG_distalROI (t) > threshold
                // store waveform propagation-time at distal location
                Td = t
        end
        if Tp and Td are both different from zero and from their previous
values
                // calculate PTT (Pulse Transit Time)
                PTT = Td - Tp
                // calculate PWV (Pulse Wave Velocity). L is provided by
                the laser point technique as described in the application
                PWV = L / PTT
                // calculate the elastic modulus
                E = ( PWV² *1059* (d²- d₀²) ) / ( d₀ * (d- d₀) )
                // calculate continuous blood pressure
                p(t) = E*d*h / d₀ (1-0.5^2) // h estimated from literature
        end
else // If counter >= 3*sampling rate
        // find the minimum amplitude in the PPG signal which is
        associated with the diastolic phase. At the end of the 3 s a
        minimum AVG_proximalROI value will be found, which will
        correspond to the diameter during the diastolic phase.
        If AVG_proximalROI (t+1) < AVG_proximalROI (t)
                d₀ = calculateArteryDiameter ( frame, pixel_per_metrics )
        end
end // If counter >= 3*sampling rate
end
```

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A contactless system for measuring and continuously monitoring arterial blood pressure, the system comprising:

one or more light sources configured to illuminate light having at least one predetermined wavelength at a predetermined area of a human subject having an artery therein;

a detector responsive to reflected light from the predetermined area configured to continuously acquire images of the artery in the predetermined area; and a processor configured to process the images of the artery and determine:

when an image of the artery at a proximal location of the predetermined area is darker indicating transition of a pulse wave into the artery at the proximal location and at a proximal time and an image at a distal location of the predetermined area is darker indicating transition of the pulse wave into the artery at the distal location at a distal time and configured to determine a length between the proximal location of the artery and the distal location of the artery as measured from the images at the proximal and distal locations.

contactlessly and continuously calculate the arterial blood pressure for each cardiac cycle of the human subject.

2. The system of claim 1 in which the at least one predetermined wavelength includes one or more wavelengths between a wavelength of green light and a wavelength of near infrared (NIR) light.

3. The system of claim 2 in which the at least one predetermined wavelength is sensitive to oxygenated and/or deoxygenated hemoglobin concentration in blood of the human subject.

4. The system of claim 1 in which the one or more light sources includes one or more near infrared (NIR) sensors.

5. The system of claim 1 in which the detector includes a charge coupled device (CCD) camera.

6. The system of claim 1 in which the one or more light sources are configured to emit spaced light to create a reference objects for the processor to determine the proximal location and the distal location.

7. The system of claim 1 further including a non-transitory computer readable storage medium coupled to the processor.

8. The system of claim 1 further including a display coupled to the processor configured to continuously display the calculated arterial blood pressure for each cardiac cycle.

9. The system of claim 8 further including a user interface coupled to the display.

10. The system of claim 1 in which the processor is further configured to perform one or more of:

determining the difference in time between the distal time and the proximal time to calculate a pulse transit time (PTT), calculating a pulse wave velocity of the pulse wave by dividing the determined length by the PTT, determining a diameter of the artery during a systolic phase of a cardiac pulse, determining a diameter of the artery during a diastolic phase of a cardiac pulse, calculating pulse pressure ($\Delta P$) using the determined diameter of the artery during a systolic phase of a cardiac pulse and the determined diameter of the artery during a diastolic phase of a cardiac pulse, calculating an elastic modulus (E) of the artery, and contactlessly and continuously calculating the arterial blood pressure for each cardiac cycle of the human subject using the calculated pulse pressure and elastic modulus.

11. A method for continuously measuring and continuously monitoring arterial blood pressure, the method comprising:

illuminating light at least one predetermined wavelength at a predetermined area of a human subject having an artery therein;

continuously acquiring images of the artery in the predetermined area from light reflected from the predetermined area;

processing the images of the artery with a processor to determine:

when an image of the artery at a proximal location of the predetermined area is darker indicating transition of a pulse wave into the artery at the proximal location and at a proximal time and when an image at a distal location of the predetermined area is darker indicating transition of the pulse wave into the artery at the distal location at a distal time and configured to determine a length between the proximal location of the artery and the distal location of the artery as measured from the images at the proximal and distal locations, and contactlessly and continuously calculate the arterial blood pressure for each cardiac cycle of the human subject.

12. The method of claim 11 in which the at least one predetermined wavelength includes one or more wavelengths between a wavelength of green light and a wavelength of near infrared (NIR) light.

13. The method of claim 11 in which the at least one predetermined wavelength is sensitive to oxygenated and/or deoxygenated hemoglobin concentration in blood of the human subject.

14. The method of claim 11 in which the illuminating light is provided by one or more near-infrared sensors.

15. The method of claim 11 including providing one or more light sources configured to emit spaced light to create reference objects for the processor to determine the proximal location and the distal location.

16. The method of claim 11 further including continuously displaying the calculated arterial blood pressure.

17. The method of claim 11 in which the processor is further configured to perform one or more of:

determining the difference in time between the distal time and the proximal time to calculate a pulse transit time (PTT), calculating a pulse wave velocity of the pulse wave by dividing the determined length by the PTT, determining a diameter of the artery during a systolic phase of a cardiac pulse, determining a diameter of the artery during a diastolic phase of a cardiac pulse, calculating pulse pressure ($\Delta P$) using the determined diameter of the artery during a systolic phase of a cardiac pulse and the determined diameter of the artery during a diastolic phase of a cardiac pulse, calculating an elastic modulus (E) of the artery, and contactlessly and continuously calculating the arterial blood pressure for each cardiac cycle of the human subject using the calculated pulse pressure and elastic modulus.

\* \* \* \* \*